(12) United States Patent
Kim et al.

(10) Patent No.: US 10,738,981 B2
(45) Date of Patent: Aug. 11, 2020

(54) LED LIGHTING DEVICE FOR MOBILE PHONE

(71) Applicant: HASS Corp., Gangneung-si, Gangwon-do (KR)

(72) Inventors: Yongsu Kim, Gangneung-si (KR); Hyunjun Jeon, Busan (KR); Kyungsik Oh, Incheon (KR); Youngpyo Hong, Gangneung-si (KR); Hyungbong Lim, Ansan-si (KR); Joonhyung Kim, Anseong-si (KR); Sungmin Kim, Yongin-si (KR); Siwon Son, Seoul (KR)

(73) Assignee: HASS CORP., Gangneung-si, Gangwon-Do (KR)

(*) Notice: Subject to any disclaimer, the term of this patent is extended or adjusted under 35 U.S.C. 154(b) by 80 days.

(21) Appl. No.: 16/198,119

(22) Filed: Nov. 21, 2018

(65) Prior Publication Data
US 2020/0158316 A1 May 21, 2020

(51) Int. Cl.
| | | |
|---|---|---|
| A61G 15/00 | (2006.01) |
| F21V 21/088 | (2006.01) |
| F21V 23/06 | (2006.01) |
| F21V 23/00 | (2015.01) |
| F21V 9/14 | (2006.01) |
| H04M 1/725 | (2006.01) |
| A61B 1/24 | (2006.01) |
| A61C 1/08 | (2006.01) |
| A61B 1/06 | (2006.01) |

(Continued)

(52) U.S. Cl.
CPC ........ *F21V 21/0885* (2013.01); *A61B 1/0684* (2013.01); *A61B 1/24* (2013.01); *A61C 1/088* (2013.01); *F21V 9/14* (2013.01); *F21V 23/003* (2013.01); *F21V 23/06* (2013.01); *H04M 1/72527* (2013.01); *F21W 2131/202* (2013.01); *F21Y 2105/18* (2016.08); *F21Y 2115/10* (2016.08)

(58) Field of Classification Search
None
See application file for complete search history.

(56) References Cited

U.S. PATENT DOCUMENTS

| | | | | |
|---|---|---|---|---|
| 2009/0046140 A1* | 2/2009 | Lashmet | ................ | G09G 3/002 348/51 |
| 2015/0318885 A1* | 11/2015 | Earle | ..................... | H04B 1/385 455/575.6 |

(Continued)

FOREIGN PATENT DOCUMENTS

| | | |
|---|---|---|
| KR | 10-0993141 | 11/2010 |
| KR | 10-2012-0114422 | 10/2012 |

(Continued)

*Primary Examiner* — Elmito Breval
(74) *Attorney, Agent, or Firm* — Kile Park Reed & Houtteman PLLC (57) ABSTRACT

The present disclosure relates to an LED lighting device for a mobile phone. The LED lighting device for a mobile phone includes a main body to which power is supplied, a fixing portion that is provided at a lower portion of the main body and is detachably coupled to a mobile phone, a lighting unit that is rotatably connected to a front of the main body and emits light when DC power is applied thereto, and a connection bar that connects the main body to the lighting unit.

5 Claims, 10 Drawing Sheets

(51) Int. Cl.
*F21W 131/202* (2006.01)
*F21Y 105/18* (2016.01)
*F21Y 115/10* (2016.01)

(56) References Cited

U.S. PATENT DOCUMENTS

2017/0319416 A1* 11/2017 Bailey .................. A61G 15/002
2018/0092534 A1* 4/2018 Nabhan ................ H04N 5/2257
2020/0011491 A1* 1/2020 Cao ........................... F21L 4/02

FOREIGN PATENT DOCUMENTS

| KR | 10-1281030 | 7/2013 |
| KR | 10-2016-0117036 | 10/2016 |

* cited by examiner

LED LIGHTING DEVICE FOR MOBILE PHONE

BACKGROUND

1. Field

The present disclosure relates to an LED lighting device for a mobile phone, and particularly, to a technology that has a color temperature and a high color rendering property similar to natural light by improving a structure of a light source, avoids color interference by using a colorless light source, prevents an irregular reflection by using a light diffusion plate, can be mounted in a plurality of mobile phones by applying a spring fixture, and can perform an efficient color analysis, an efficient management of picture data, and color reproduction of a practitioner by using an application.

2. Description of the Related Art

In recent years, various mobile communication devices have become popular due to development of the Internet, and particularly, mobile phones such as smart phones are widely used.

In addition, the mobile phone has various functions besides a telephone function mounted therein due to development of an IT technology, thereby being used in various fields.

For example, the mobile phone is used in a field of dentistry, which treats teeth or manufactures a prosthetic steel.

That is, lighting levels differ from each other for each working area, in an area where collaboration is required for color management, such as a dental clinic, a dental laboratory, an apparel designer, and a textile company, and thereby, there are many communication inconveniences in communication where a target color is distinguished and job details are discussed due to the a difference between a color temperature and a color rendering property, and a difference between illuminations.

Such a lighting device includes a lighting device such as a halogen lamp, a halogen-tungsten lamp, or a fluorescent lamp capable of emitting light of a high intensity ranging from 1,500 lux to 2,500 lux.

By using the lighting capable of emitting the light of a high intensity, a space for shadowing in a work space is minimized.

However, the lighting devices such as a halogen lamp, a halogen-tungsten lamp, and a fluorescent lamp are distant from a standard required in a dental field in a color temperature, a color rendering index, and illumination. The dental field requires illumination of a color temperature of 5,500K and a color rendering index of 90 Ra or more, but there is a problem that a generally used lighting device such as a halogen lamp, a halogen-tungsten lamp, or a fluorescent lamp does not satisfy the standard.

Here, the color temperature represents a color of light emitted from a light source as a temperature, which is represented as an absolute temperature. The lower the color temperature, the higher the ratio of red color, and the higher the color temperature, the higher the ratio of blue color. All objects are shined and colored by light. The color of an object changes depending on the color temperature and wavelength of light shining on the object.

Natural light around noon has a color temperature of approximately 5,500K, and when light having a color temperature of approximately 5,500K is projected on an object, the object will have a color similar to a color seen in natural light.

However, in general, a halogen lamp has a color temperature of 2,900K to 3,000K, thereby, having a red color, and a fluorescent lamp has a color temperature of 4,000K thereby having a yellow color. Therefore, there is a problem that, when such a light is projected on teeth, the tooth cannot have its own color.

A color rendering index (CRI) is a numerical representation of how much the color of an object seen in natural light is similar to the color seen in a specific illumination. The CRI is represented in units of 0 Ra to 100 Ra, and the closer to 100Ra, the closer the illumination is to natural color.

In a case of a halogen lamp, the color rendering index is in the range of 95 Ra to 100 Ra and does not satisfy a color temperature condition. In a case of a fluorescent lamp, the color rendering index is only approximately 70 Ra to 80 Ra and is far from a criterion required in an industrial field in which a color analysis work is important.

In addition, a lighting device in the related art, such as a halogen lamp, a halogen-tungsten lamp, or a fluorescent lamp emits a diffused light, and thereby, there is a problem in which a space for shadow increases in a work space, a diffused reflection is generated, and it is difficult to distinguish an internal color of a tooth in a case of a dental clinic.

Meanwhile, a color of an artificial tooth is adjusted to be most closely to a tooth of a patient with reference to a picture of the tooth of the patient taken in a dental office when constructing the artificial tooth in a dental laboratory, and the artificial tooth is made with reference to a brief description of a production request.

As described above, a color of the tooth is represented differently depending on the type of light that is projected on the tooth. In many cases, the illumination used in a dental office and the illumination used in the dental laboratory are different from each other in characteristics.

Therefore, in a case where the artificial tooth is made at a dental laboratory with reference to a picture of a patient taken at the dental office, there is a problem that the color of the made artificial tooth is often inconsistent with the color of the patient's tooth.

In addition, even in a case of illuminance indicating brightness of illumination, a mobile phone has to located close to a light source at the time of close-up photographing due to the nature of the mobile phone. In this case, an irregular reflection to an object to be photographed may be made, and thereby, a problem occurs in which a proper illumination is hard to maintain.

SUMMARY OF THE DISCLOSURE

The present disclosure is to provide an LED lighting device for a mobile phone close to natural light and a mobile application thererfor, thereby, providing an efficient communication between a work requester and a work practitioner.

In addition, the present disclosure is to provide an LED lighting device for a mobile phone that can prevent a shadow and a diffused reflection from occurring when observing a patient's teeth in a dental office and can clearly distinguish an internal color of the teeth.

In addition, the present disclosure is to provide an LED lighting device that can prevent an error in which a color of an artificial tooth is inconsistent with color of a patient's tooth from occurring when the artificial tooth is made in a dental laboratory by matching characteristics of illumination and a color determination criterion which are used in a dental office and a dental laboratory to each other.

In addition, the present disclosure is to provide an LED lighting device that can be widely used in a field relating to a color work in many different industries in addition to a dental clinic and dental engineering, prevents a color operation error from occurring due to lighting devices in different work spaces of a work requester and a work practitioner, facilitates transmission of job details via a memo function of an application and voice recording of a moving picture, and can prevent rework and improve work efficiency by efficiently storing and managing data.

According to one embodiment of the present disclosure, there is provided an LED lighting device for a mobile phone including a main body to which power is supplied, a fixing portion that is provided at a lower portion of the main body and is detachably coupled to a mobile phone, a lighting unit that is rotatably connected to a front of the main body and emits light when DC power is applied thereto, and a connection bar that connects the main body to the lighting unit.

The lighting unit includes a base that is mounted in a tip of the connection bar, a pair of LED mounting portions that are movably mounted on the base to emit light and have a ring shape, LED packages that are arranged on the pair of LED mounting portions to emit light, a pair of guide bars that are arranged in a radial direction from the base and movably support the pair of LED mounting portions inwardly or outwardly in the radial direction; and a power control unit that controls power sources of the LED packages.

The LED lighting device for a mobile phone according to one embodiment of the present disclosure has the following advantages.

First, an LED light source, which emits light close to natural light (5,500K) with a color temperature of 5,500K to 5,700K and a color rendering index of 90 Ra or more and with illumination of 650 Lux to 700 Lux at a distance of 10 cm from the light source, can be effectively used for a color reproduction work in many industrial fields.

Second, by using an LED lighting device for a mobile phone with a high straightness and a light diffusion plate, it is possible to prevent shadow and diffused reflection from being generated when observing a patient's tooth in a dental office and to clearly distinguish an inner color of the tooth.

Third, since an LED lighting device for a mobile phone and a mobile application with the same characteristics can be used in a dental office and a dental laboratory, it is possible to provide accuracy and efficiency in manufacture of an esthetic prosthesis by preventing an error in which a color of an artificial tooth is inconsistent with a color of a patient's tooth due to a difference in lighting used in a dental office and a dental laboratory when making the artificial tooth in the dental laboratory.

Fourth, when analyzing a reference color of a light source, it is advantageous to perform the color analysis through an annular structure of a ring type, and when imaging an object, in a case where a contour of the object is clearly taken by a symmetrically divided light source of twin type and practice is done by exchanging the data, a smooth communication is made between a work requester and a work practitioner, and work efficiency can be increased by preventing rework.

Fifth, if the color of a patient's tooth is accurately distinguished by using a natural light-specific mobile light source in a dental office and a color analysis is performed by using an application and other data necessary for making an artificial tooth is also transferred to a dental laboratory by using imaging and editing functions, it is possible to accurately distinguish the color of a patient's tooth at the dental laboratory and to make the artificial tooth faithful to requirements of the dental office which is a client.

Sixth, since DC power is used as the power of a light source, it is possible to prevent flickering from being generated to accurately observe a color of a tooth by using.

Seventh, it is possible to use the LED light device according to the present disclosure for mobile phones of various sizes by applying a fixing portion of a spring type.

DETAILED DESCRIPTION OF THE EMBODIMENT

Hereinafter, an LED lighting device for a mobile phone according to an embodiment of the present disclosure will be described in detail with reference to the accompanying drawings.

Figure 1:
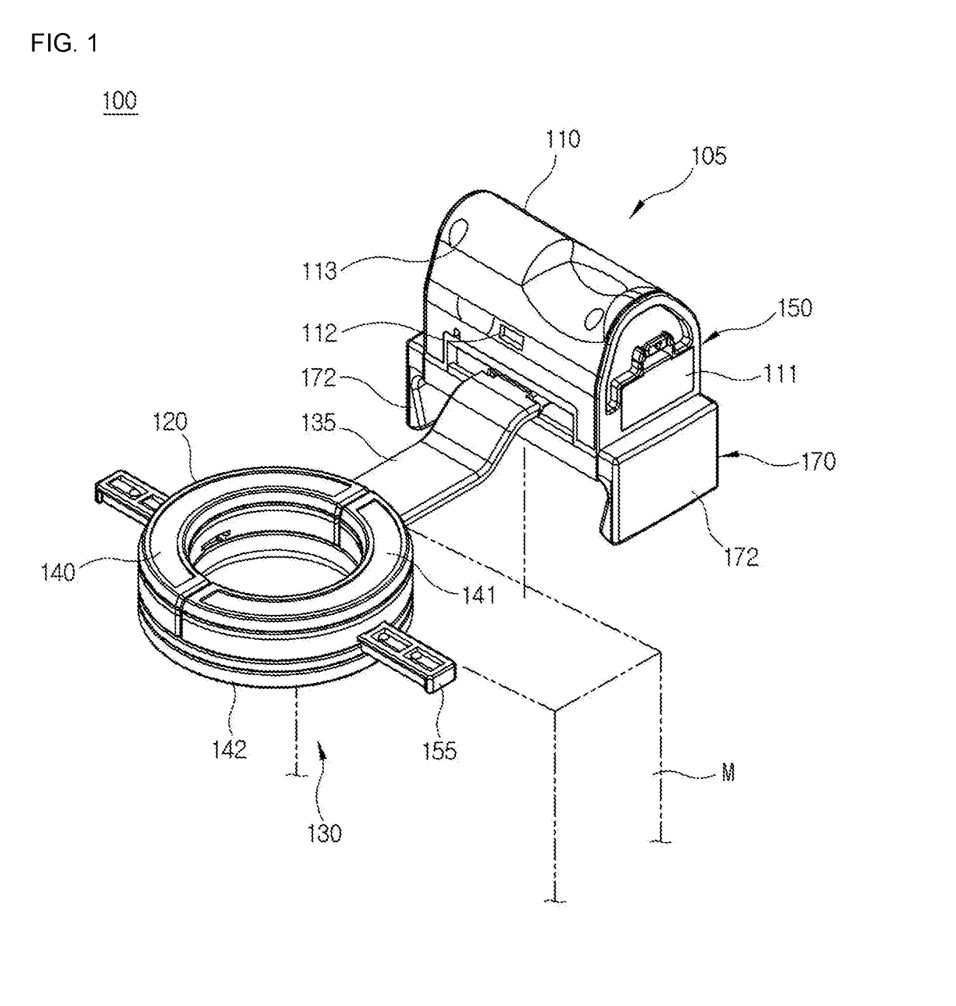
FIG. 1 is a perspective view of an LED lighting device for a mobile phone according to an embodiment of the present disclosure.
Figure 2:
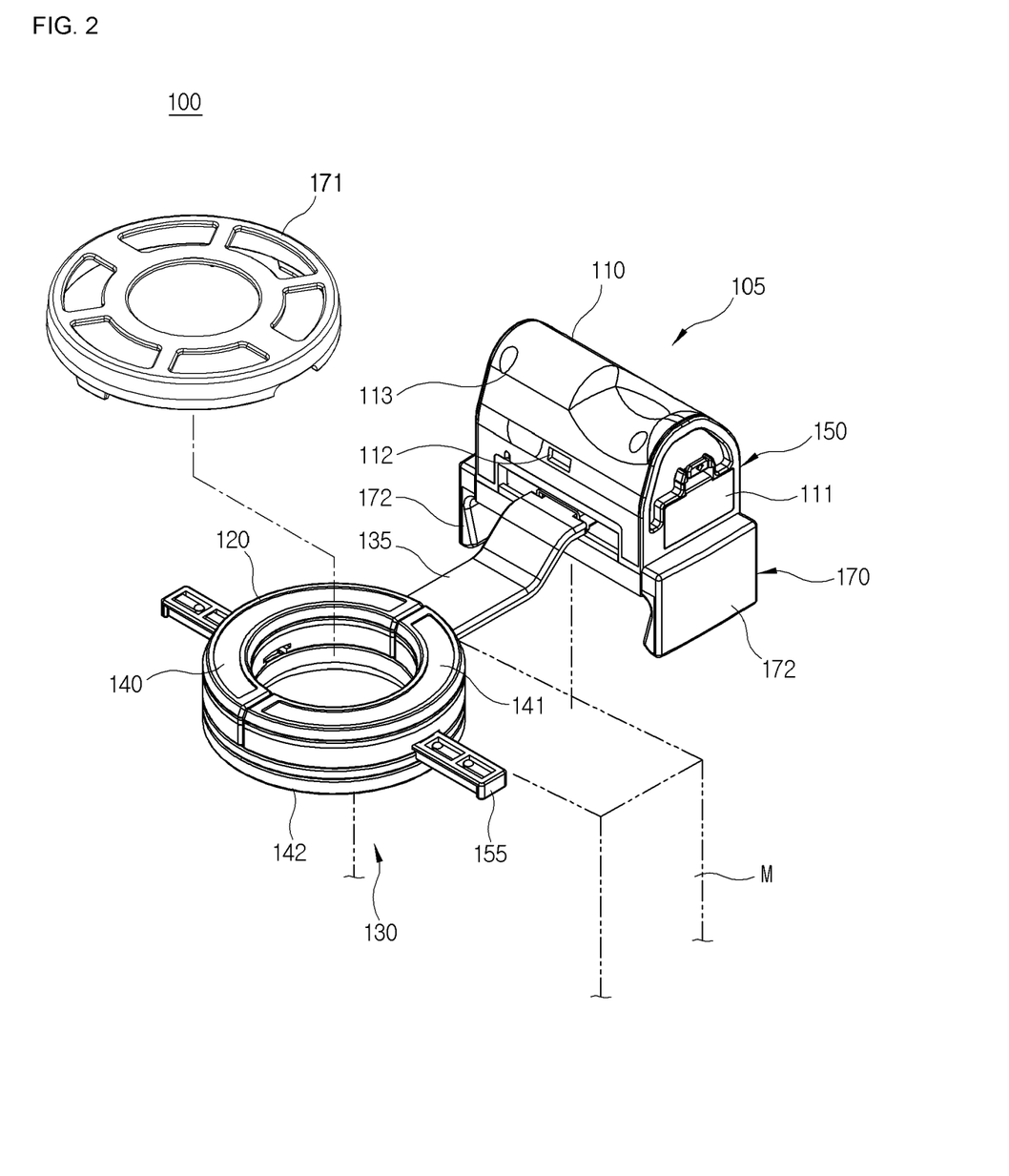
FIG. 2 is a view illustrating a structure in which a polarization filter is mounted as another embodiment of the LED lighting device illustrated in FIG. 1.
Figure 3:
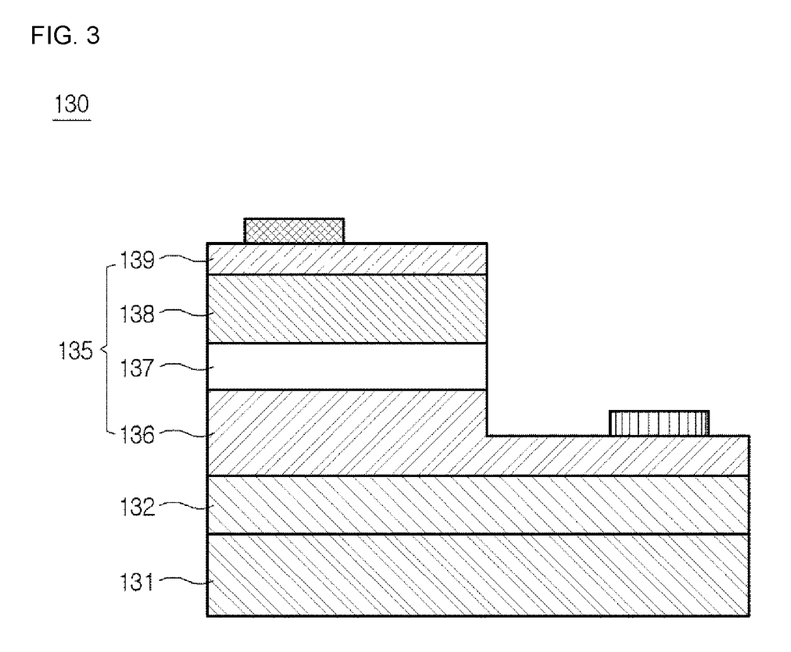
FIG. 3 is a cross-sectional view illustrating an LED element used in the LED lighting device for a mobile phone illustrated in FIG. 1.

As illustrated in FIGS. 1 to 3, an LED lighting device 100 according to the present disclosure may be used in various fields, and a case where the LED lighting device 100 is used in a dental clinic and a dental field will be described as an example.

The LED lighting device 100 for a mobile phone includes a main body 105 in which a power source, a power terminal, and a switch are disposed; a fixing portion 170 that is provided at a lower portion of the main body 105 and is detachably coupled to a mobile phone M; a lighting unit 130 that is connected to the front of the main body 105 and emits light; and a connection bar 135 that connects the main body 105 to the lighting unit 130.

In the LED lighting device 100 for a mobile phone having such a structure, the main body 105 is provided with a handle 110 such that a user may grasp. A power source unit 150 for supplying power is provided inside the handle 110.

At this time, various types of power supply methods may be applied to the power source unit 150, and preferably include a method of supplying power from a battery 111. The battery 111 supplies DC power and the DC power is supplied to the lighting unit 130 via a power terminal 112.

As described above, since the DC power is supplied to the lighting unit 130, flickering may be eliminated when observing a patient's teeth, and thereby, a color of the patient's teeth may be accurately observed.

In addition, a power switch 113 is provided on a side surface of the main body 105 to turn on or off the power of the lighting unit 130.

In addition, the fixing portion 170 may be provided at a lower portion of the handle 110 to be detachably coupled to an upper portion of the mobile phone.

At this time, the fixing portion 170 may have a spring structure such that the fixing portion 170 may be combined with mobile phones of various sizes.

That is, the fixing portion 170 is configured with a pair of fixing plates 172, and a spring (not illustrated) is disposed between the pair of fixing plates 172 in a lateral direction. The spring elastically pulls the pair of fixing plates 172 inwardly.

Therefore, in order to fix the lighting device for a mobile phone to an upper portion of the mobile phone M, the pair of fixing plates 172 is pulled to both sides, the fixing plates 172 is mounted on the upper portion of the mobile phone M, the pulling force is released, and thereby, the fixing plate 172 returns to an original position due to a restoring force of the spring to be fixed.

Meanwhile, the lighting unit 130 includes a base 142 mounted in a tip of the connection bar 135; a pair of LED mounting portions 120 which are movably mounted on the base 142 and emit light; LED packages 140 disposed on the pair of LED mounting portions 120 to emit light; a pair of guide bars 155 that are arranged in the radial direction from the base 142 and support movably the pair of LED mounting portions 120 inwardly or outwardly in the radial direction; and a power control unit 160 that controls power sources of the LED packages 140.

In more detail, the base 142 is circularly disposed in the tip of the connection bar 135 to support the LED mounting portions 120.

In addition, a pair of guide bars 155 are arranged outwardly in the radial direction in the base 142.

In addition, the pair of LED mounting portions 120 have a hollow ring shape. In addition, the pair of LED mounting portions 120 are configured with the two LED mounting portions 120, each having a semi-circular shape, and are movable separately from each other.

Accordingly, the pair of LED mounting portions 120 may move inwardly or outwardly along the pair of guide bars 155.

At this time, the pair of LED mounting portions 120 may be coupled to the upper portions of the pair of guide bars 155 in various movable manners such as a male and female coupling.

Figure 8:
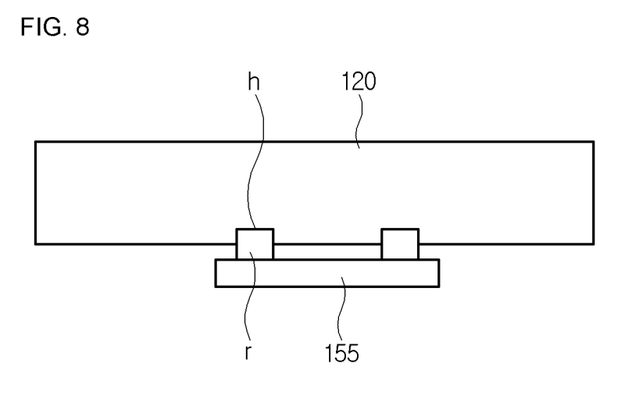
FIG. 8 is a view illustrating a state in which the LED mounting portion illustrated in FIG. 1 is slidably coupled to a guide bar.

For example, as illustrated in FIG. 8, guide grooves h are formed in a bottom surface of the LED mounting portion 120, and the guide grooves h are coupled with guide rails r formed on the pair of guide bars 155.

Accordingly, the guide grooves h of the LED mounting portions 120 may be moved inwardly or outwardly in the radial direction in a state in which the guide grooves are coupled with the guide rails r of the guide bar 155.

As such, since the pair of LED mounting portions 120 may move inwardly and outwardly along the guide bar 155, a position of the LED mounting portion 120 may be appropriately changed depending on an illumination environment or the like and may be imaged.

Figure 9A:
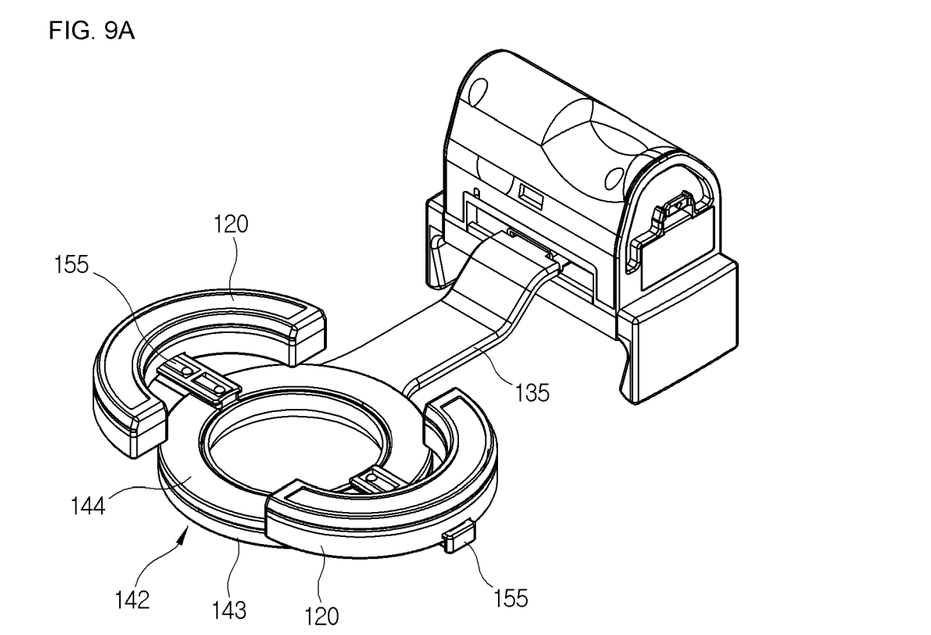
FIG. 9A is a view illustrating a state in which the LED mounting portion moves outwardly in a radial direction and is rotated 90 degrees.
Figure 9B:
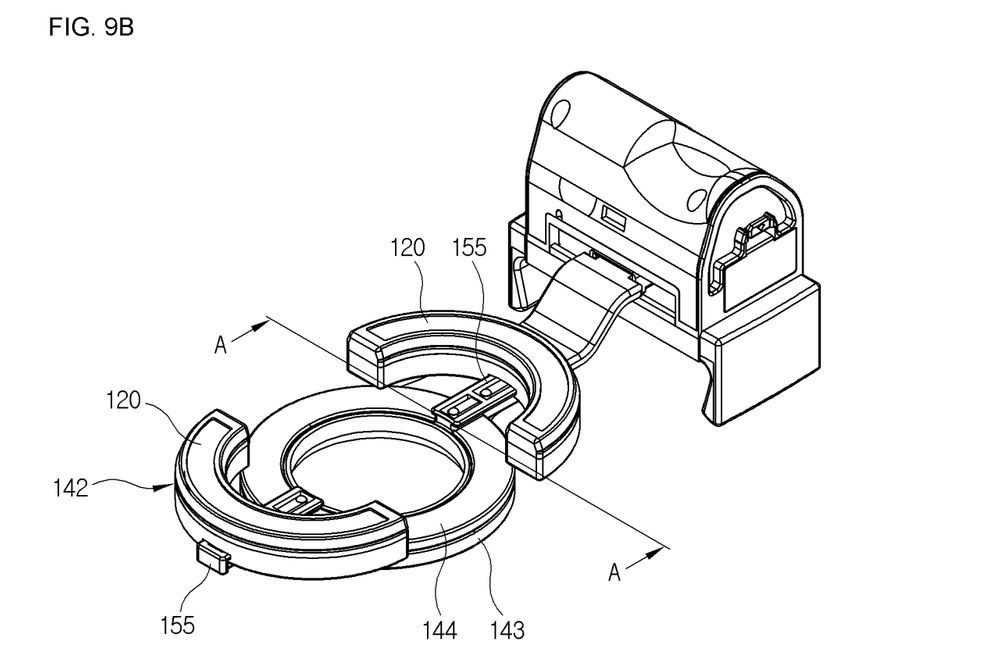
FIG. 9B is a view illustrating a state in which the LED mounting portion forms a circle and is rotated 90 degrees.

In addition, as illustrated in FIGS. 9A and 9B, the pair of LED mounting portions 120 are rotatable by 90 degrees.

More specifically, the base 142 is connected to the tip of the connection bar 135, and the base has a two-layer structure.

That is, the base includes a lower base 143 connected to the tip of the connection bar 135, and an upper base 144 which is rotatably disposed on an upper portion of the lower base 143 and on which a pair of guide bars are mounted.

Figure 10:
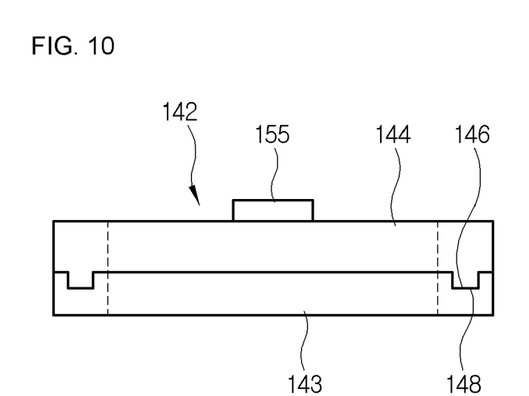
FIG. 10 is a view taken along line A-A in FIG. 9B.

In the base 142, a guide groove 148 is formed in the upper surface of the lower base 143 in a circumferential direction, a rail 146 protrudes from an upper surface of the upper base 144, and the rail 146 is rotatably coupled with the guide groove 148.

Accordingly, the rail 146 of the upper base 144 may rotate along the guide groove 148 of the lower base 143. Of course, in the above description, it is described that the rail protrudes from the upper base 144 and the guide groove is formed in the lower base 143, and the present disclosure is not limited thereto, and the rail and the guide groove may be disposed reversely. That is, the guide groove may be formed in the upper base and the rail may be formed in the lower base.

Alternatively, as a bearing is disposed between the upper base and the lower base, the upper base may be configured in a rotatable manner.

As such, in a case where the upper base 144 rotates, the pair of guide bars 155 mounted thereon also rotate, and accordingly, the pair of LED mounting portions 120 mounted on the pair of guide bars 155 may rotate together.

As a result, an illumination angle of the lighting unit 130 may be changed to 90 degrees by rotating the LED mounting unit 120 by 90 degrees.

In addition, the illumination angle may be variously changed by moving the respective LED mounting portions 120 in the radial direction along the guide bars 155 while rotating the LED mounting portions 120 by 90 degrees.

Accordingly, it is possible to appropriately adjust the illumination angle in the horizontal direction or the vertical direction depending on image capturing purposes.

In addition, the plurality of LED packages 140 are mounted on the respective LED mounting portions 120 in an annular shape. A structure in which six LED packages 140 are mounted on the LED mounting portion 120 is described in the present embodiment, the present disclosure is not limited to this, and the six LED packages 140 or more may be mounted or the six LED packages 140 or less may be mounted.

In addition, the lighting unit 130 is formed in an achromatic color as a whole. The reason why the LED lighting device 100 for a mobile phone is formed in an achromatic color is that, when a color of a tooth is distinguished by using the light of the LED lighting device 100 for a mobile phone, a color of the LED lighting device 100 is prevented from interfering with an original color of the tooth.

In addition, a light diffusion plate 141 is mounted on outer circumferential surfaces of the LED packages 140.

The light diffusion plate 141 diffuses the light emitted from an LED element 130, thereby, preventing an irregular reflection which may be generated on a tooth surface when a straight light is applied to the tooth and preventing the tooth surface in which the irregular reflection is generated from being imaged when imaging the tooth.

At this time, the LED package 140 preferably emits white light.

In another embodiment of the present disclosure, a polarization filter 170 may be mounted on an upper portion of the LED package 140, as illustrated in FIG. 2.

The polarization filter 170 allows the light to proceed in only one direction. Accordingly, effects are obtained in which unnecessarily reflected light is removed to make an object clearly visible, a flare appearing on a glossy surface is removed, and a color is not changed.

As illustrated in FIG. 3, an LED element mounted on the LED package 140 will be described. First, a nitride semiconductor 135 is stacked on a substrate 131.

Here, the nitride semiconductor 135 is configured to include an n-type semiconductor layer 136, an active layer 137, and a p-type semiconductor layer 138.

At this time, a buffer layer 132 may be formed between the nitride semiconductor 135 and the substrate 131. The buffer layer 132 may be formed of a low-temperature growth GaN layer, an AlN layer, or the like to mitigate a difference in lattice mismatching and thermal expansion coefficient of a material.

The active layer 137 has a multi-quantum well (MQW) structure and may be formed of GaN or InGaN.

The p-type semiconductor layer 138 is formed of a nitride semiconductor substance having a $Al_xIn_yGa(1-x-y)N$ composition formula (where $0>x \leq 1$, $0 \leq y \leq 1$, $0 \leq x+y \leq 1$) in the same manner as the n-type semiconductor layer 141 and is p-doped.

Meanwhile, a transparent electrode 139 is formed on the p-type semiconductor layer 138 in order to improve ohmic characteristics, and a p-electrode is formed on an upper portion of the transparent electrode.

Then, an n-electrode is formed on the etched and exposed n-type semiconductor layer.

If voltages are applied to the p-electrode and the n-electrode of the LED element 130, electrons supplied from the n-type semiconductor layer and holes supplied from the p-type semiconductor layer flow into the active layer having a different indium composition, the electrons and the holes recombine together in the active layer, and thereby, white light is emitted.

At this time, a color of the emitted light is greatly changed depending on the amount of currents flowing through the LED element 130. If a small amount of currents flow through the LED element 130, the electrons and the holes mainly combine together in a region where the indium composition is relatively large, and thereby, red light having a small energy and a long wavelength may be mainly emitted. If a large amount of currents flow, the electrons and the holes mainly combine together in a region where the indium composition is relatively small, and thereby, blue light having a large energy and a short wavelength may be mainly emitted.

Figure 4A:
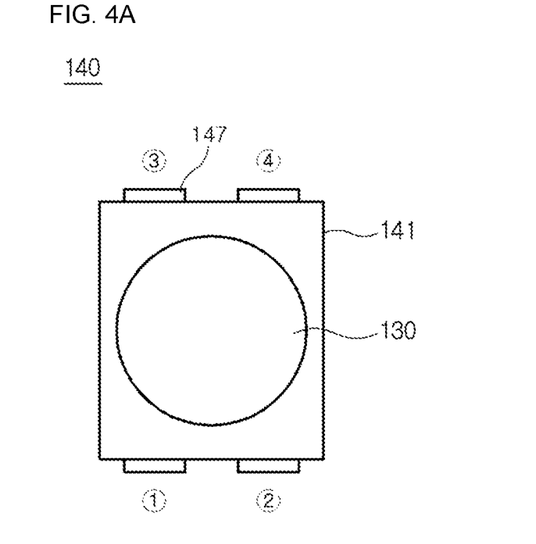
FIG. 4A illustrates an LED package for use in the LED lighting device for a mobile phone.
Figure 4B:
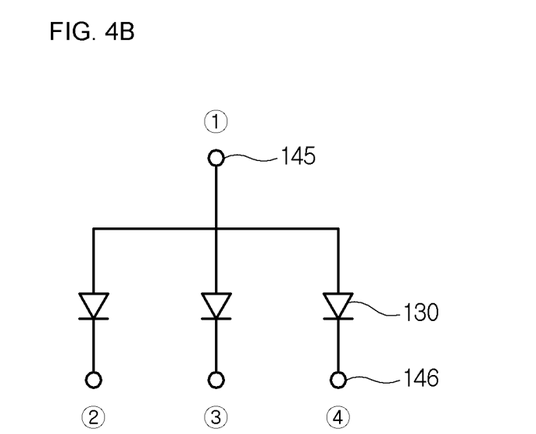
FIG. 4B illustrates the LED package and a circuit diagram thereof.

FIG. 4A illustrates the LED package 140 in which the LED element 130 is used for the LED lighting device 100 for a mobile phone, and FIG. 4B illustrates the LED package 140 and a circuit diagram thereof.

At this time, in a case where the LED package 140 is used for the LED lighting device 100 for a mobile phone, three LED elements 130 are packaged to form one LED package 140.

At this time, the LED package 140 is manufactured by arranging the three LED elements 130 on the substrate 141 and then connecting the LED elements to terminals 147.

At this time, as illustrated in the circuit diagram, anodes 145 of the three LED elements 130 are commonly used and cathodes 146 thereof are used separately.

Figure 5:
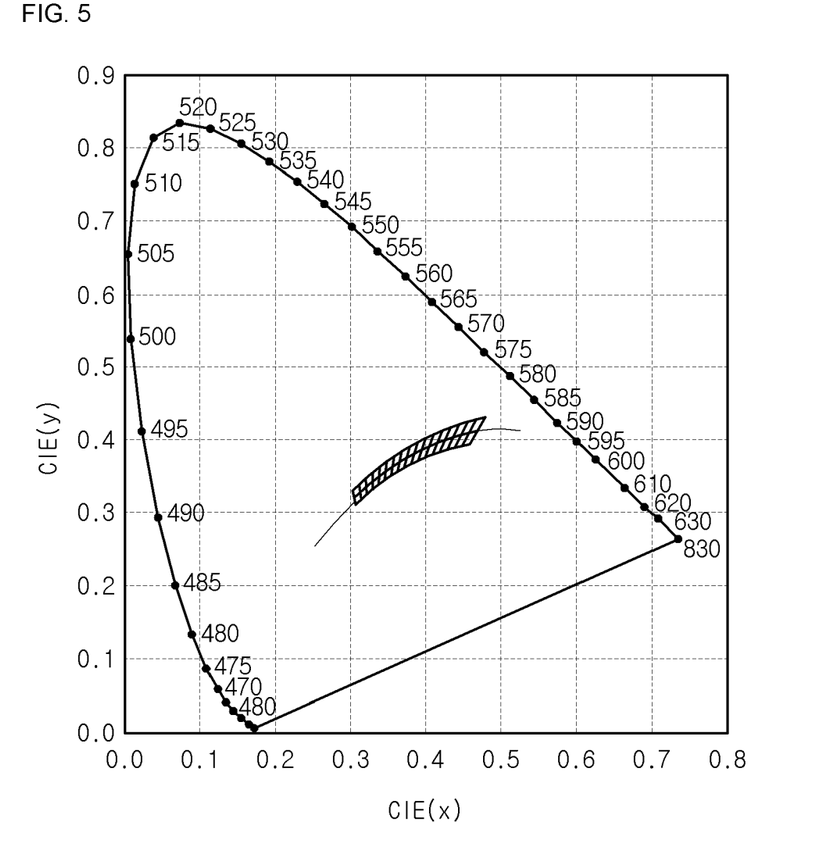
FIG. 5 is a graph illustrating a change in color temperature of light emitted from the LED element on a blackbody radiation line according to the amount of current applied to the LED element.
Figure 6:
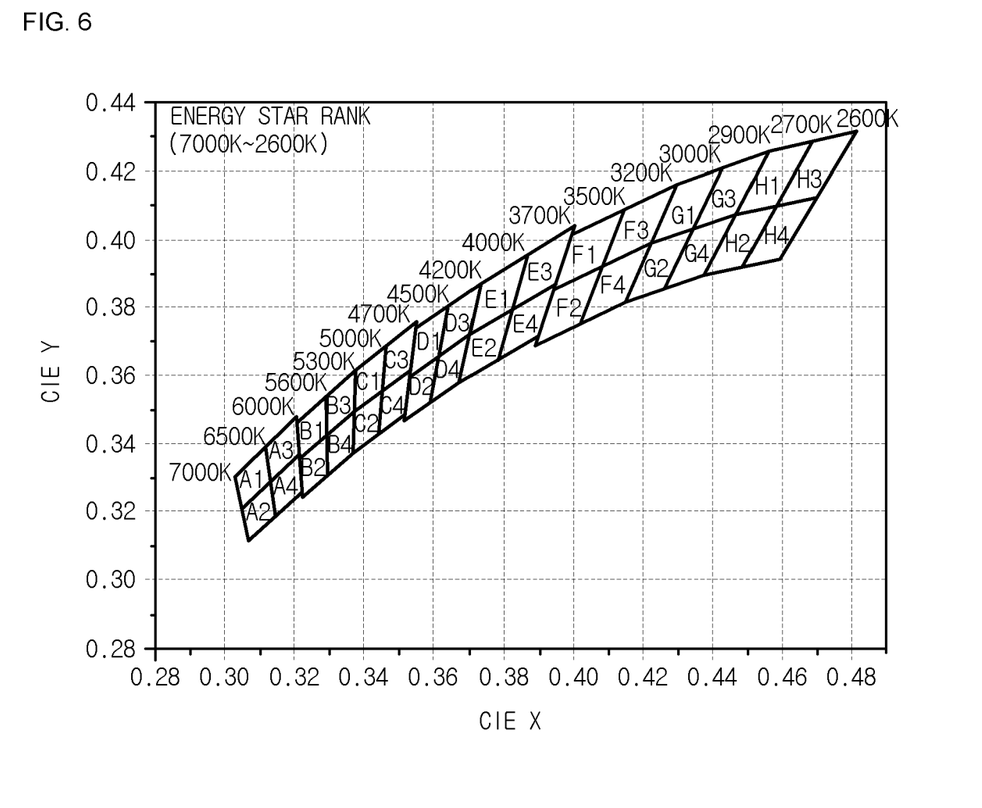
FIG. 6 is an enlarged diagram illustrating the vicinity of the blackbody radiation line in FIG. 5.

FIG. 5 is a graph illustrating a change in color temperature of light emitted from the LED element on a blackbody radiation line depending on the amount of currents applied to the LED element, and FIG. 6 is an enlarged diagram of the vicinity of the blackbody radiation line in FIG. 5.

As illustrated in the drawings, if a small amount of currents flow through the LED element 130, red light having a low color temperature is mainly emitted. If a large amount of currents flow through the LED element 130, blue light having a high color temperature is mainly emitted.

In addition, a B3 region and a B4 region have color temperatures of 5300K to 5600K in the vicinity of the blackbody radiation line.

In the LED package 140 used for the LED lighting device 100 for a mobile phone, a positive voltage of approximately 2.9 V, preferably 2.9 V, is applied to each of the LED elements 130, and it was found in experiments that, when a current of 10 mA flowed through the LED element 130, light close to a daylight color (5550K) was emitted from a B3 region and a B4 region of the LED element 130.

At this time, it was found that the current of 30 mA flows through one LED package 140 and the one LED package 140 emits light having a color rendering index of approximately 90 Ra.

Accordingly, the LED lighting device 100 for a mobile phone according to the present disclosure includes a circuit that allows a current of 10 mA to flow through the LED element 130.

Figure 7:
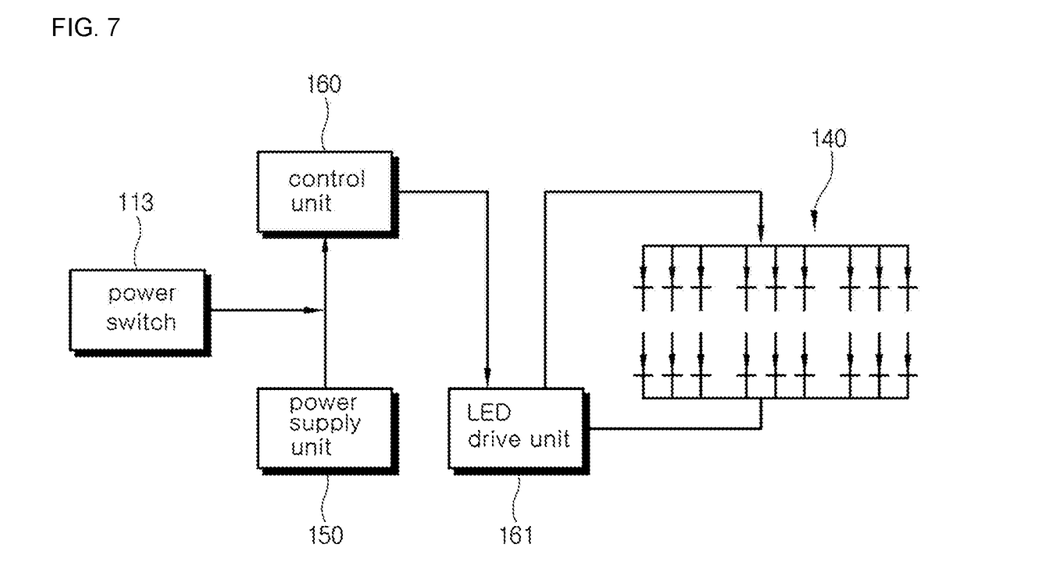
FIG. 7 is a circuit diagram of the LED lighting device for a mobile phone illustrated in FIG. 1.

FIG. 7 is a circuit diagram of the LED lighting device for a mobile phone illustrated in FIG. 1.

As illustrated in FIG. 7, the LED lighting device 100 for a mobile phone includes a power supply switch 113, a power supply unit 150 that supplies power to various components installed in the LED lighting device 100 for a mobile phone, a control unit 160 that supplies the power suitable for the LED element to drive the LED package 140 in accordance with the power of the power supply unit 150, and an LED drive unit 161 that drives the LED element in accordance with a signal of the control unit 160.

The control unit 160 controls a power supply by using a pulse frequency modulation (PFM) operation mode of 2.0 MHz switching frequency so as to supply power suitable for the LED drive unit 161, and the LED drive unit 161 controls a current which is supplied to the LED package 140 such that a current of 10 mA flows through the LED element 130.

Under the above-described control, the LED lighting device 100 for a mobile phone may emit light close to the daylight color (5500K).

INDUSTRIAL APPLICABILITY

The present disclosure relates to an LED lighting device for a mobile phone, and particularly, to a technology that has a color temperature and a high color rendering property similar to natural light by improving a structure of a light source, avoids color interference by using a colorless light source, prevents an irregular reflection by using a light diffusion plate, may be mounted in a plurality of mobile phones by applying a spring fixture, and may perform an efficient color analysis, an efficient management of picture data, and color reproduction of a practitioner by using an application. The present disclosure is applicable to a lighting industry field.

What is claimed is:
1. An LED lighting device for a mobile phone comprising:
a main body to which power is supplied;

a fixing portion that is provided at a lower portion of the main body and is detachably coupled to a mobile phone;

a lighting unit that is rotatably connected to a front of the main body and emits light when DC power is applied thereto; and a connection bar that connects the main body to the lighting unit, wherein the lighting unit includes a base that is mounted in a tip of the connection bar;

a pair of LED mounting portions that are movably mounted on the base to emit light and have a ring shape;

LED packages that are arranged on the pair of LED mounting portions to emit light;

a pair of guide bars that are arranged in a radial direction from the base and movably support the pair of LED mounting portions inwardly or outwardly in the radial direction; and a power control unit that controls power sources of the LED packages.

2. The LED lighting device for a mobile phone according to claim 1, wherein the base includes a lower base which is connected to the tip of the connection bar, and an upper base which is rotatably disposed on the lower base and on which a pair of guide bars are mounted, and wherein a guide groove is formed on the upper surface of the lower base in a circumferential direction, a rail protrudes from the upper surface of the upper base to be rotatably coupled to the guide groove, and the upper base is rotatable with respect to the lower base.

3. The LED lighting device for a mobile phone according to claim 1, wherein guide grooves are formed on bottom surfaces of the pair of LED mounting portions, and the guide grooves are slidably coupled to upper surfaces of the pair of guide bars.

4. The LED lighting device for a mobile phone according to claim 1, wherein the fixing portion includes a pair of fixing plates, and a spring that is disposed between the pair of fixing plates to elastically pull the fixing plates inwardly.

5. The LED lighting device for a mobile phone according to claim 1, wherein polarization filters are further mounted on upper portions of the LED packages.

* * * * *